(12) United States Patent
Martzel

(10) Patent No.: US 10,925,318 B2
(45) Date of Patent: Feb. 23, 2021

(54) METHOD OF CONTROLLING A VAPING DEVICE AND VAPING DEVICE FOR CARRYING OUT THE METHOD

(71) Applicant: SARL GAIATREND, SARL, Rohrbach-lès-Bitche (FR)

(72) Inventor: Didier Martzel, Rohrbach-lès-Bitche (FR)

(73) Assignee: SARL GAIATREND, SARL, Rohrbach-lès-Bitche (FR)

( * ) Notice: Subject to any disclaimer, the term of this patent is extended or adjusted under 35 U.S.C. 154(b) by 283 days.

(21) Appl. No.: 16/097,884

(22) PCT Filed: May 2, 2017

(86) PCT No.: PCT/EP2017/060438
§ 371 (c)(1),
(2) Date: Oct. 31, 2018

(87) PCT Pub. No.: WO2017/191143
PCT Pub. Date: Nov. 9, 2017

(65) Prior Publication Data
US 2019/0142067 A1    May 16, 2019

(30) Foreign Application Priority Data

May 2, 2016 (FR) ...................................... 1653951

(51) Int. Cl.
*A24F 47/00*    (2020.01)
*A61M 11/04*    (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .............................. A24F 40/50; A24F 47/008
See application file for complete search history.

(56) References Cited

U.S. PATENT DOCUMENTS

| 5,894,841 | A | 4/1999 | Voges |
| 8,550,069 | B2 | 10/2013 | Alelov |

(Continued)

FOREIGN PATENT DOCUMENTS

| AU | 2006269882 A1 | 1/2007 |
| CN | 1788806 A | 6/2006 |

(Continued)

OTHER PUBLICATIONS

International Search Report and Written Opinion dated Jun. 5, 2018 issued in corresponding application No. PCT/EP2017/060438; w/ English partial translation and partial machine translation (24 pages).

(Continued)

*Primary Examiner* — Eric Yaary
(74) *Attorney, Agent, or Firm* — Seckel IP, PLLC

(57) ABSTRACT

The method of controlling a vaping device including a power source, a reservoir for a liquid, an atomizer for vaporizing the liquid into an aerosol, an aspiration sensor, and a control unit, has the following steps: (a) testing to detect activation of the vaping device, and proceeding to step (b) when the vaping device is activated; (b) testing to detect the presence of aspiration of a puff, and proceeding to step (c) as soon as aspiration of a puff has been detected; (c) monitoring a first control event during each puff, and returning to step (b) if the first control event has not occurred, or continuing to step (d) if it has occurred; and (d) placing the vaping device on standby as soon as the first control event has occurred. An aerosol can be generated for an aspiration when the device is activated, but not when it is on standby.

27 Claims, 6 Drawing Sheets

(51) Int. Cl.
*A61M 15/06* (2006.01)
*A61M 16/00* (2006.01)

(52) U.S. Cl.
CPC ............... *A61M 2016/0021* (2013.01); *A61M 2205/3368* (2013.01)

(56) References Cited

U.S. PATENT DOCUMENTS

| | | |
|---|---|---|
| 2007/0283972 A1 | 12/2007 | Monsees et al. |
| 2009/0260641 A1 | 10/2009 | Monsees et al. |
| 2009/0260642 A1 | 10/2009 | Monsees et al. |
| 2011/0010029 A1 | 1/2011 | Seel et al. |
| 2012/0048266 A1 | 3/2012 | Alelov |
| 2013/0042865 A1 | 2/2013 | Monsees et al. |
| 2013/0306084 A1* | 11/2013 | Flick ................. A24F 40/50 131/328 |
| 2013/0312742 A1 | 11/2013 | Monsees et al. |
| 2013/0333712 A1* | 12/2013 | Scatterday ........... A61M 11/042 131/329 |
| 2015/0020833 A1 | 1/2015 | Conley et al. |
| 2015/0150308 A1 | 6/2015 | Monsees et al. |
| 2015/0216237 A1* | 8/2015 | Wensley ............. H05B 1/0244 131/273 |
| 2015/0245654 A1* | 9/2015 | Memari ................. H02J 50/10 141/2 |
| 2015/0288468 A1* | 10/2015 | Xiang ................... A24F 47/008 455/500 |
| 2015/0313284 A1* | 11/2015 | Liu .......................... A24F 40/40 131/329 |
| 2016/0089508 A1* | 3/2016 | Smith ............... A61M 15/0003 128/200.16 |
| 2016/0242466 A1* | 8/2016 | Lord ..................... H05B 1/0202 |
| 2016/0374400 A1 | 12/2016 | Monsees et al. |
| 2017/0079331 A1 | 3/2017 | Monsees et al. |
| 2017/0245547 A1* | 8/2017 | Lipowicz ............. H05B 1/0222 |
| 2020/0221759 A1 | 7/2020 | Monsees et al. |

FOREIGN PATENT DOCUMENTS

| | | |
|---|---|---|
| WO | 2007012007 A3 | 1/2007 |
| WO | 2007/077067 A1 | 7/2007 |
| WO | 2013/025921 A1 | 2/2013 |

OTHER PUBLICATIONS

Chinese Office Action and Search Report dated Oct. 10, 2020 in counterpart application No. CN 201780027355.1; with English translation (total 15 pages) (D1, US2015020833 cited in the Chinese Office Action is not listed in this IDS since it was already listed in the IDS filed Oct. 31, 2018).

* cited by examiner

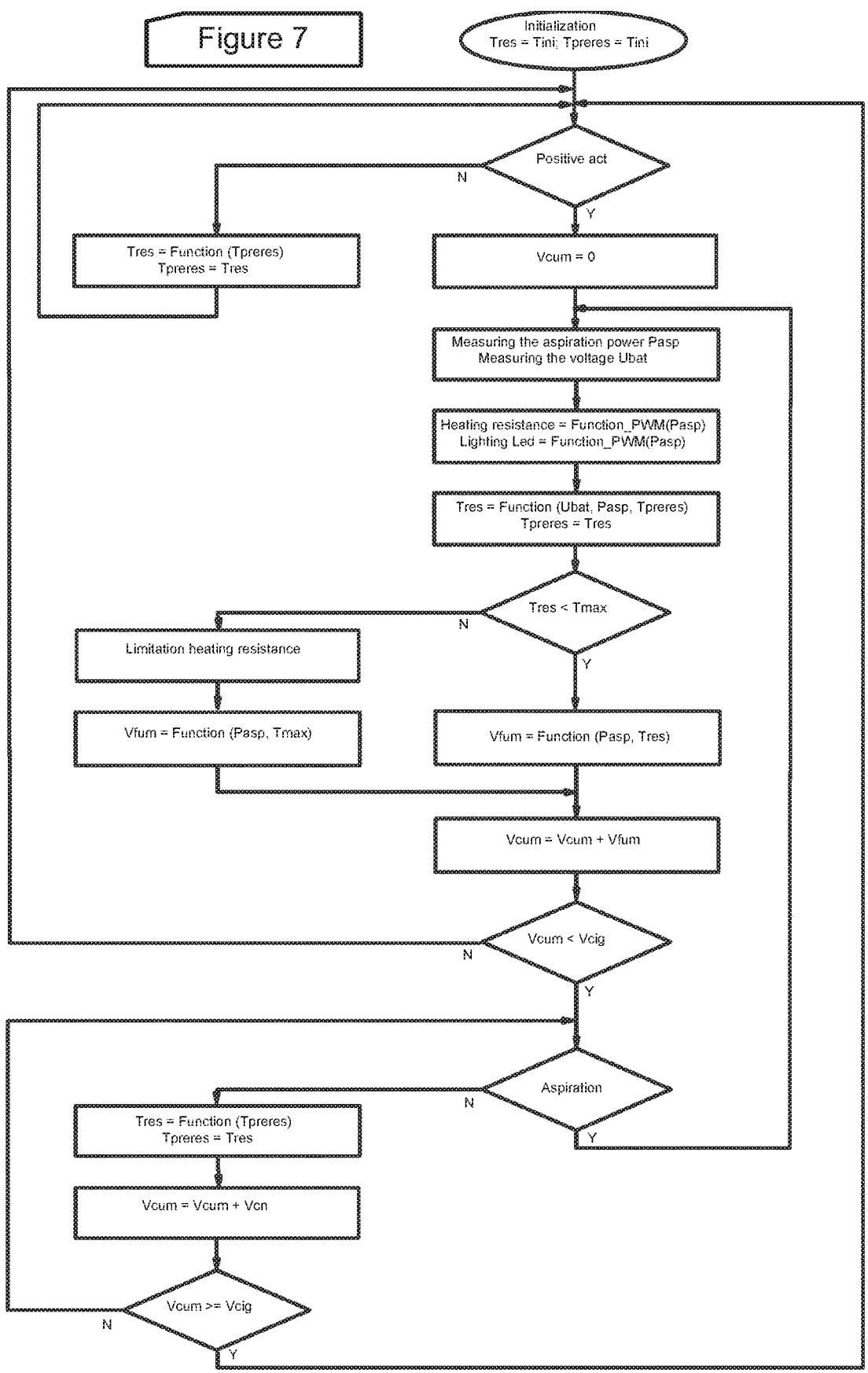

METHOD OF CONTROLLING A VAPING DEVICE AND VAPING DEVICE FOR CARRYING OUT THE METHOD

TECHNICAL FIELD

The invention relates to an inhalation device of the vaping type provided with control means comprising means for activating the vaping device, means for determining a control event and means for placing the vaping device on standby when the control event has occurred. The invention also relates to a method of controlling such a device.

By vaping device, it is meant in particular electronic cigarettes or e-cigarettes, electronic shishas, electronic cigars, electronic cigarillos, electronic pipes and more generally the devices which, by heating a liquid, called e-liquid, generate an aerosol for inhalation and are intended in particular to be used as substitutes for products containing smoking tobacco. They can also be used for inhaling medical products.

PRIOR ART

Vaping devices are increasingly common and contribute to help people quit smoking. The different vaping devices operate in the same manner and differ essentially only in their outer shape. The following description will be done based on the example of the e-cigarette, but it can be transposed to all other types of vaping devices.

These vaping devices generally comprise the following elements:
- a source of electrical energy such as an accumulator, a battery, or even a connection to the mains;
- a cartridge containing the e-liquid that serves to generate the aerosol and that contains various additives such as propylene glycol, flavorings, or nicotine;
- an atomizer, which is generally constituted by a heating resistance designed for vaporizing at low temperature the e-liquid from the cartridge;
- a microprocessor to manage the different parameters during use of the vaping device;
- an under-pressure sensor that detects the times when the vaper draws a puff and that sends a signal to the microprocessor so that it turns on the atomizer; and
- a LED that serves, either simply to indicate that the vaping device is activated, or to represent a point of incandescence simulating the combustion of tobacco.

It is common for the cartridge and the atomizer to be combined into a single element called "cartomizer" or "clearomizer". The e-cigarette is generally, either in standby mode when it is not used, or in active mode when the user uses it.

The consumer starts by filling the reservoir or cartomizer and verifies that the battery is sufficiently charged. Either he manually turns on the electronic cigarette by pressing a button, or the electronic cigarette is automatically switched on at the first aspiration, which the microprocessor detects using the under-pressure sensor. The microprocessor then activates the heating resistance and turns on the LED. As soon as the liquid reaches about 60° C., an aerosol is formed, which is aspirated by the vaper. If the liquid contains a substance having a recognized effect, such as nicotine, this substance is inhaled by the vaper. Since the nicotine-containing aerosol is formed without combustion, the e-cigarettes is considered a good alternative to traditional cigarettes to help quit smoking tobacco.

With a traditional cigarette, the smoker receives a dose of nicotine with each puff until the cigarette has been fully consumed. Some smokers draw frantically and at short intervals on their cigarettes, while others draw less strongly and take their time, letting the cigarette burn by itself between puffs. Thus, a same cigarette does not provide the same amount of nicotine depending on how it is smoked. However, each person, according to his mode of consumption, knows approximately the number of cigarettes he smokes daily. A cigarette is thus a kind of measurement unit specific to each person.

Unlike a traditional cigarette, an e-cigarette does not burn up. It is therefore possible to take only a few puffs from time to time, which would correspond to only a fraction of a cigarette. But it is also possible to draw many more puffs than would have been possible with a traditional cigarette. Thus, vapers often face the problem of "continuous vaping". As a consequence, it is difficult to know precisely the amount of nicotine inhaled during a day. A vaper may therefore find himself in a nicotine overdose without really realizing it. It has been observed that the e-cigarette makes it easier to stop the traditional cigarette, but not to stop nicotine.

Some manufacturers have thus designed e-cigarettes that can only operate during some well-defined periods. Outside of these periods, the e-cigarette remains inert. Another solution consists in requiring a positive action from the vaper so that he is conscious of his gesture. For example, patent application WO2007/077167A1 can be cited, which describes an electronic cigarette that turns on only after the vaper has lighted it with the flame of a lighter, like a traditional cigarette.

The objective of the invention is to restore signs to which tobacco smokers are used, in order to help them re-accustom themselves to the notion of the "cigarette" unit. Another objective is to control the dose of medicament absorbed by a patient, when the method is applied to an inhalation device for medical use, as well as to respect intervals between two successive intakes.

DISCLOSURE OF THE INVENTION

These objects are achieved with the control method of the invention, which provides the following steps:
(a) testing to detect the activation of the inhalation device, and proceeding to step (b) as soon as the activation of the inhalation device is detected
(b) testing to detect the presence of the aspiration of a puff, and proceeding to step (c) as soon as the aspiration of a puff is detected,
(c) monitoring a first control event during each puff, and returning to step (b) if the first control event does not occur, or continuing to step (d) if the first control event has occurred,
(d) placing the vaping device on standby,
wherein an aerosol can be generated in the event of an aspiration when the device is activated, but not when it is on standby.

It may be useful to inform the user that the first event has occurred. For this purpose, it can be provided that a signal is emitted in step (d) when the device is placed on standby.

This control method can be supplemented by a second control during the pauses between each puff. For this purpose, in step (b), after each test that has concluded to the absence of an aspiration, that is to say, during each pause between two successive puffs or between the activation and the first puff, a second control event, identical to or different from the first control event, is monitored, and the method continues directly at step (d) if the second control event has occurred.

In the medical field, it is common that medicaments must be administered at regular intervals. Not respecting these intervals can have serious consequences for the patient, whether the drugs are taken too close in time or the prescribed interval is exceeded. In order to avoid intakes that are too close together, it can be interesting to prevent the reactivation of the inhaler until a certain time interval has elapsed between two intakes. Taking the example of a drug that must be taken every four hours, a time delay, called blocking time delay, can be provided, which prevents the reactivation of the inhaler less than four hours after the previous placement into standby mode. This same principle can be applied to a vaping device to force the vaper to wait a while before starting to use the vaping device again. Thus, the method can provide that the inhalation device can be activated in step (a) only after a minimum time interval, called blocking interval (Delay1, Delay2) has elapsed since the preceding activation in step (a) or since the preceding placement on standby in step (d) or since a predefined action was performed. In some cases, especially for medicaments, it is also possible to control, not the time between the placement on standby and the next reactivation, but between two successive activations. Thus, a patient would begin to take a dose of medication every 4 hours for example, regardless of the time it took to take the preceding dose.

Also with a view toward helping a patient respect the intervals between two intakes, it may be useful to remind him that it is time to take the next dose. For this purpose, it can be provided to trigger a second time delay after expiration of the time delay that prevented the inhalation device from activating, which, when it comes to an end, triggers the emission of a signal that warns the patient that he has not yet taken the current dose. This time delay can reboot automatically after each expiration until the inhalation device is activated, for example by a first aspiration. To this end, it can be provided that after expiry of the blocking interval (Delay1, Delay2), a signal is emitted at regular intervals, called reminder intervals (tlima), as long as the inhalation device has not been activated in step (a).

In a preferred embodiment of the invention, it is provided to determine the volume of aerosol generated during each aspiration, to cumulate these volumes in the course of the consumption of the vaping or inhalation device, and to compare this cumulative volume to a reference volume corresponding to the volume that a corresponding conventional smoking device (cigarette, cigar, pipe, shisha, etc.) would have generated, or to the volume corresponding to a dose of a medicament. As soon as the accumulated volume reaches the reference volume, the vaping device goes into standby, thus indicating to the vaper that he has finished his "cigarette" or to the patient that he has absorbed the prescribed dose. Thus, reaching the reference volume constitutes the first event. For this purpose, the step (c) comprises the following sub-steps performed at each passage at step (c):

(c1) determining the generated volume of aerosol (Vfum(i)) during the present passage (i) of step (c), (c2) calculating the cumulative volume of aerosol (Vcum(i)) by adding, to the cumulative volume (Vcum(i−1)) of the preceding passage (i−1) of step (a, b or c), the generated volume of aerosol (Vfum(i)) during the present passage of step (c), wherein the cumulative volume (Vcum(0)) at the activation of the vaping device has the value 0, and (c3) comparing the cumulative volume (Vcum(i)) to a predefined threshold volume (Vcig), the method then continuing at the beginning of step (b), that is to say, at the test of the presence of an aspiration, if the cumulative volume (Vcum(i)) is less than the threshold volume (Vcig), or the method continuing at step (d) if the cumulative volume (Vcum(i)) is greater than or equal to the threshold volume (Vcig).

When the method is applied to tobacco substitutes, such as electronic cigarettes, for example, it can be provided to calculate, during each pause, a fictitious volume of aerosol corresponding to the volume of smoke that would have been generated by a traditional cigarette through slow consummation between two aspirations. This fictitious volume is added to the cumulative volume of aerosol generated during the aspirations, then this cumulated volume is compared to the threshold volume. The vaping device is placed on standby as soon as the threshold volume is reached. It is thus possible that the vaping device goes into standby during a pause. For this purpose, the step (b) can comprise the following sub-steps performed after each test in step (b) that has determined the absence of an aspiration, that is to say, during a pause between two successive aspirations:

(b1) determining a fictitious volume of aerosol (Vcn(i)) corresponding to the present passage (i) of step (b), (b2) calculating the cumulative volume (Vcum(i)) of the volumes of aerosol generated previously during aspirations and of the fictitious volumes generated previously during pauses by adding, to the cumulative volume (Vcum(i−1)) of the preceding passage (i−1) of step (a, b or c), the fictitious volume of aerosol (Vcn(i)) of the present passage (i) of step (b), wherein the cumulative volume (Vcum(0)) at the activation of the vaping device has the value 0, (b3) comparing the cumulative volume (Vcum(i)) to the predefined threshold volume (Vcig), the method continuing at the beginning of step (b), that is to say, at the test of the presence of an aspiration, if the cumulative volume (Vcum(i)) is less than the threshold volume, or the method continuing at step (d) if the cumulative volume (Vcum(i)) is greater than or equal to the threshold volume (Vcig).

In practice, it can be considered that the fictitious volume of aerosol (Vcn(i)) by the passage of step (b) during the pauses is constant (Vcn).

The cumulative volume can be calculated and compared to the threshold value at the end of each aspiration or of each pause, each defining a time interval whose duration varies from one aspiration to the other, and from one pause to the other. However, it is preferable to calculate the cumulative volume (Vcum(i)) and to compare it to the threshold volume (Vcig) several times per aspiration or per pause. This will allow in particular placing the vaping device on standby after a long pause, without waiting for the vaper to try to draw a puff long after the control volume has reached the threshold value during the last pause. In this case, the time intervals depend on the frequency of the clock present in the control unit that manages the vaping device.

When the method is used to administer a medicament, calculating a fictitious volume of smoke is no longer meaningful. However, it may be useful to limit the time available to take the dose of the drug. If, after a certain prefixed time, the quantity of drug absorbed (Vcum(i)) has not reached the prescribed dose (Vcig), it may be useful to stop the intake of the drug and thus to place the inhalation device on standby. For this purpose, it can be provided that step (b) comprises the following steps, performed at each passage of step (b), after each test that has determined the absence of an aspiration:

(b1') determining the duration ($t(i)$) of the present passage (i) of step (b), (b2') calculating the cumulative duration ($tcum_b(i)$) of all the passages of step (b) during which the method determines the absence of an aspiration by adding, to the cumulative duration ($tcum_b(i-1)$) of the preceding passage (i−1) of step (b), the duration ($t(i)$) of the present passage of step (b), wherein the cumulative duration ($tcum_b(0)$) at the time of activation of the device inhalation has the value 0, (b3') comparing the cumulative duration ($tcum_b(i)$) to a predefined threshold duration ($tlim_b$), the method continuing at the beginning of step (b) if the cumulative duration ($tcum_b(i)$) is less than the threshold duration ($tlim_b$), or the method continuing at step (d) if the cumulative duration ($tcumb(i)$) is greater than or equal to the threshold duration ($tlim_b$).

In practice, it can be considered that the duration ($t(i)$) of a passage of step (b) during the pauses is constant ($t$).

It is preferable to calculate the cumulative duration ($tcum_b(i)$) and to compare it to the threshold duration ($tlim_b$) several times per pause. This will allow in particular placing the inhalation device on standby after a long pause, without waiting for the patient to try to draw a new puff long after the preceding one. In this case, the durations ($t(i)$) of each passages of step (b) can be defined to be all identical. Since the inhalation device will go into standby state without the amount of medicament absorbed ($Vcum(i)$) having reached the prescribed dose ($Vcig$), it is preferable that the patient, a third party responsible for monitoring the good taking of the medication, or a monitoring process be notified of this default in the intake by the emission of a signal.

A time delay can also be provided to prevent the patient from reactivating the inhalation device until a certain time interval has elapsed since the placement on standby or since the last activation. Thus, a first blocking time delay (Delay1) can be provided after the placement on standby in step (d), when the cumulative volume ($Vcum(i)$) is greater than or equal to the threshold volume ($Vcig$), and a second blocking time delay (Delay2) can be provided after the placement on standby in step (d) after expiry of the threshold control duration ($tlim_b$), the duration of the second time delay (Delay2) preferably being equal to the duration of the first time delay (Delay1) minus the threshold control duration ($tlim_b$).

The generated volumes of aerosol can be measured or estimated using more easily measurable parameters. For example, one can provide in step (c1) to determine the aspiration power ($Pasp(i)$) of the present passage (i) of step (c), preferably using an aspiration sensor, and/or to determine the temperature of the atomizer ($Tres(i)$) of the present passage (i) of step (c), then to calculate the generated volume of aerosol ($Vfum(i)$) during the present passage (i) of step (c) as a function of the aspiration power ($Pasp(i)$) and/or of the temperature of the atomizer ($Tres(i)$).

In order to prevent the atomizer temperature from exceeding a certain temperature threshold beyond which harmful products might be emitted, it is preferable, at each passage (i) of step (c) during the aspirations, to determine the temperature of the atomizer ($Tres(i)$) and to compare it to a threshold value ($Tmax$), wherein heating of the atomizer is limited if the temperature of the atomizer ($Tres(i)$) is greater than the threshold value ($Tmax$).

The temperature of the atomizer can be either measured or determined using other measurable or determinable parameters. But then, the more powerful the aspiration, the more the atomizer is heated and the more the temperature rises. When the space within the inhalation device or its configuration allow it, it is preferable to use a temperature sensor. However, in vaping devices, it is difficult to use such a sensor. Indeed, the cartomizer is an interchangeable part which is screwed into the electronic cigarette. Thus, it is not easy to ensure contact between a temperature sensor located inside the cartomizer and the microprocessor of the e-cigarette. In this case, it is preferable to estimate the temperature as a function, on the one hand, of the initial temperature, and on the other hand, of the aspiration power, of the duration of the aspiration, and of the voltage across the power source. Thus, it is possible to provide the following steps:

after activation of the vaping device,
the temperature of the atomizer is set at a predetermined value ($Tres(0)$);
then during each aspiration at each passage (i) of step (c), the aspiration power ($Pasp(i)$) is determined, preferably using an aspiration sensor,
the voltage ($Ubat(i)$) at the terminals of the electrical power source is measured,
the temperature of the atomizer ($Tres(i)$) is determined, on the one hand, as a function of the temperature of the atomizer ($Tres(i-1)$) at the preceding passage (i−1) of step (a, b or c), and on the other hand, as a function of the aspiration power ($Pasp(i)$) and of the voltage at the terminals of the power source ($Ubat(i)$);
during each pause between aspirations and/or during standby mode, at each passage (i) of step (a) or (b),
the temperature of the atomizer ($Tres(i)$) is determined as a function of the temperature of the atomizer ($Tres(i-1)$) at the preceding passage (i−1) of step (a, b or c).

Vaping devices are generally provided with a light source such as a LED, to indicate to the vaper that his device is activated. It is preferable that the light source be lit during each aspiration. The luminous intensity of the light source at each passage (i) of step (c) can depend on the aspiration power ($Pasp(i)$) and/or the light source can progressively go out at the end of each aspiration and/or the light source can be powered by a signal whose pulse width is modulated (PWM).

The activation of the vaping device in step (a) can be triggered, for example, by pressing a switch and/or automatically by taking the vaping device out of a casing and/or at the first aspiration and/or after a heat source, preferably a flame, has been approached to a detector arranged in the vaping device. If activation is triggered by a first aspiration, then the first pause, the time between the activation and the first aspiration, is directly over.

Heating of the atomizer can be controlled by a signal whose pulse width is modulated (PWM).

In order to prevent the vaper from circumventing the control method by reactivating the vaping device as soon as it has gone into standby, it is preferable that the activation of the vaping device in step (a) cannot be triggered until after a minimum time interval has elapsed since the previous placing on standby or until after a predefined action has been performed. For example, it can be provided that the vaping device must be stored in a casing.

When activation of the inhalation device in step (a) is triggered by taking the inhalation device out of a casing, it can be preferable to provide a counter which is incremented each time the inhalation device is put back into the casing after at least one aspiration has been detected. In this case, the counter can be reset once a day and the counter value can be displayed on a screen placed on the inhalation device and/or the casing.

More generally, it is preferable to provide a counter which is incremented each time the method passes in step (d). This counter can be reset once a day and the counter value can be displayed on a screen placed on the inhalation device and/or the casing.

The invention also relates to a vaping device comprising an electrical power source, a reservoir for a liquid to be vaporized, an atomizer for vaporizing the liquid to generate an aerosol, an aspiration sensor and a control unit, wherein the reservoir and the atomizer can be combined into a single component. The device of the invention is characterized in that the control unit is provided with means to implement the method of the invention.

The inhalation device is preferably equipped with a screen adapted to display statistical data, for example information about the amount of generated volumes of aerosol (Vfum) during a predefined unit of time or about the number of times the method has passed in step (d) per a unit of time, preferably information about the amount of generated volumes of aerosol (Vfum) per day or information about the number of times per day the method has passed in step (d). This is to inform the vaper of the number of "cigarette equivalents" that were vaped during the day, or to inform the patient of the number of doses absorbed during the day. It can be provided to indicate the daily total of aerosol volumes that were actually absorbed, which is useful when the objective is to know the daily amount of nicotine or the amount of medicament absorbed, or the daily total of the absorbed volumes and of the fictitious volumes when the vaper must refer to a "cigarette equivalent".

The vaping device can be provided with a casing in which it can be stored. This casing can be used simply as storage and recharge box. It can also be used to control the consumption of the e-cigarette. In this case, a screen can be provided on the inhalation device and/or on the casing. This screen can be designed to display statistical data, preferably information about the amount of generated volumes of aerosol (Vfum) during a predefined unit of time or about the number of times the method has passed in step (d) per a time unit, preferably information about the amount of generated volumes of aerosol (Vfum) per day or information about the number of times per day the method has passed in step (d). Here also, it can be provided to indicate the daily total of the volumes of aerosol that were actually absorbed, which can be useful when the objective is to know the daily amount of nicotine or the amount of medicament absorbed, or the daily total of the absorbed volumes and of the fictitious volumes when the vaper must refer to a "cigarette equivalent".

More generally, the inhalation device can be provided with a counter which is incremented each time the method passes in step (d). In this case, the counter is preferably reset once daily and the counter value is preferably displayed on a screen placed on the inhalation device and/or the casing.

BRIEF DESCRIPTION OF THE DRAWINGS

An embodiment of the method according to the invention is described below using the following figures:
FIG. 7: detailed flowchart for activation by another positive act (turning on the device using a flame, pressing a button, etc.).

MANNERS OF CARRYING OUT THE INVENTION

Figure 1:
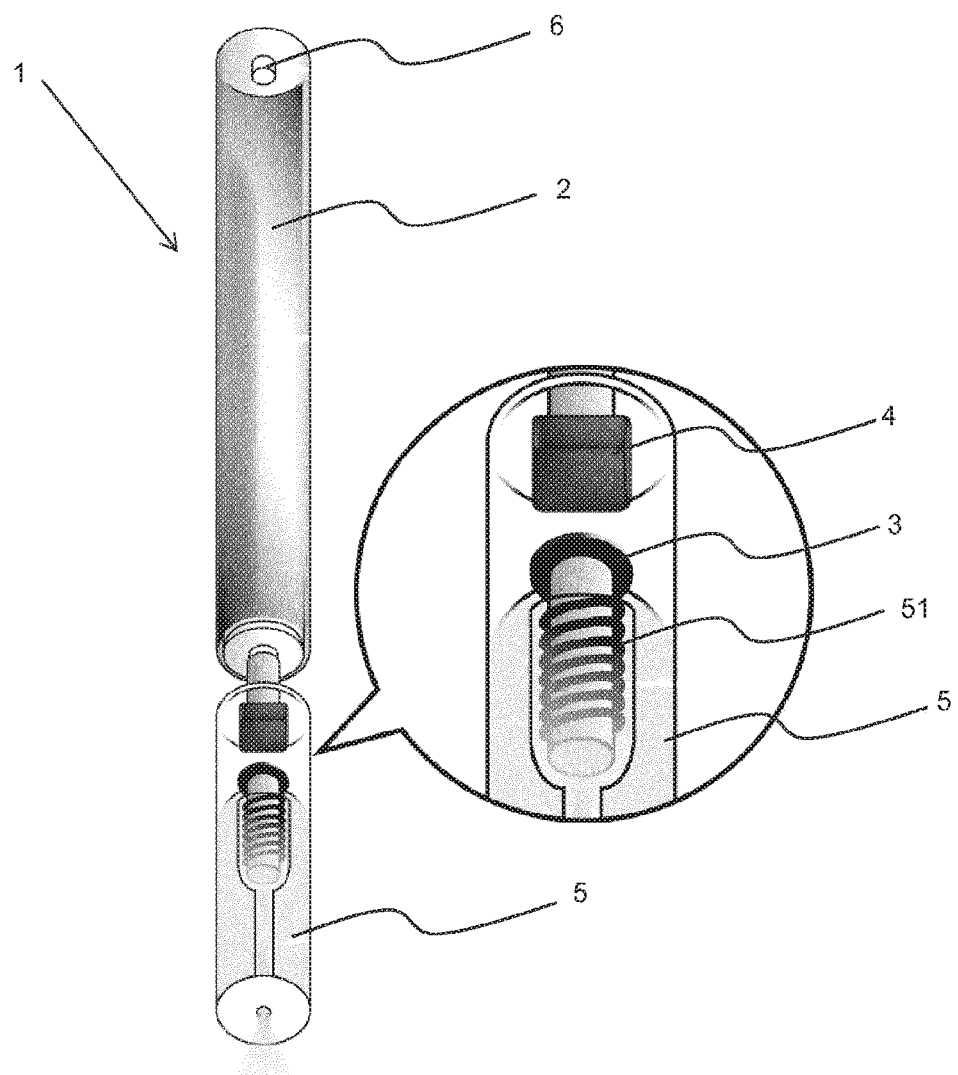
FIG. 1: schematic diagram of an e-cigarette.

The invention relates to an electronic inhalation device of the vaping type. A vaping device is understood as an aerosol generator serving as a substitute for a tobacco product, such as a cigarette, cigar, cigarillo, a pipe or a shisha. These vaping devices include in particular electronic cigarettes (or e-cigarettes), electronic cigarillos, electronic cigars, electronic pipes and electronic shishas. The method also applies to the administration of medicaments in the form of an aerosol generated by evaporation of a liquid. For simplicity, the inhalation device will be referred to as "vaping device" or "e-cigarette", without this term being limitative.

All these vaping devices (1) have essentially the same elements and differ from each other mainly in their outer shape. They include in particular:
a source of electrical power (2),
a reservoir for a liquid to be vaporized (commonly called e-liquid),
an atomizer for vaporizing the liquid in order to generate an aerosol,
an aspiration sensor (3) and
a control unit (4) provided with a microprocessor and a clock.

It is common that the reservoir and the atomizer are combined into a single component commonly called "cartomizer" or "clearomizer" (5). These elements serve to transform the liquid into an aerosol. For this purpose, they are equipped with a heat source, such as a heating resistance (51). This heat source is switched on during aspiration. The longer the aspiration lasts, the more the heat source heats up and the larger the generated volume of aerosol. Particularly in the case of devices serving as tobacco substitutes, the cartomizer is a removable part that is screwed into the body of the e-cigarette. Indeed, e-liquids are often flavored, so it is preferable, in order to avoid mixing them, to have one cartomizer per flavor, or even per nicotine concentration.

Generally, the electrical power source is a rechargeable accumulator (2). But it can also be constituted by a battery, or even an external source, such as utility power. In order to show the vaper that the vaping device is warming up, the vaping device is often provided with a light source such as a LED (6), which lights up when the vaper draws a puff and the atomizer or cartomizer is supplied by the power source. This LED can be placed at the end opposite to the mouthpiece and simulate embers of tobacco in the process of smoldering.

FIG. 1 shows, as an example, an electronic cigarette or e-cigarette, with its various components. The following description is based on the example of such an e-cigarette. However, the method could also be transposed to any other type of vaping device or more generally to any type of electronic inhalation device adapted to generate an aerosol by vaporization of a liquid.

After being lighted by a flame, a traditional cigarette burns until tobacco exhaustion. The consummation occurs, either in an accelerated manner, when the smoker draws a puff, or more slowly, between two puffs. Thus, volumes of smoke due to the aspiration and volumes of smoke due to the slow consummation are produced. The volume of smoke due to aspiration depends on the duration and power of the aspiration. Furthermore, the more powerful the aspiration, the higher the temperature of the embers, and the greater the volume of smoke generated. The amount of remaining tobacco decreases accordingly. The slow consummation, meanwhile, is regular and depends only on the duration of the pause.

Figure 2:
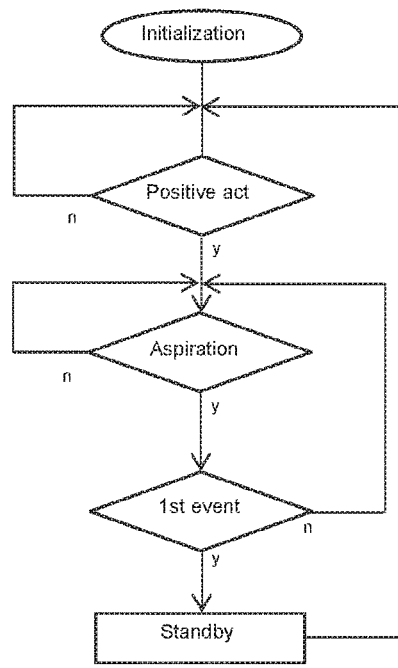
FIG. 2: basic flowchart of the control method according to the invention.

The objective of the invention is to provide a method of controlling an e-cigarette which approximates this consummation process of a traditional cigarette. A decision is made on a first event to be monitored, and as soon as this first event has occurred, the microprocessor causes the e-cigarette to go into standby. The control of this first event can be performed during aspirations (FIG. 2).

This basic method is thus characterized by the following steps:

(a) testing to detect the activation of the inhalation device, and proceeding to step (b) as soon as the activation of the inhalation device is detected, (b) testing to detect the presence of the aspiration of a puff, and proceeding to step (c) as soon as the aspiration of a puff is detected, (c) monitoring a first control event during each puff, and returning to step (b) if the first control event has not occurred, or continuing to step (d) if the first event control has occurred, (d) placing the inhalation device on standby, wherein an aerosol can be generated in the event of an aspiration when the device is activated, but not when it is on standby.

Figure 3:
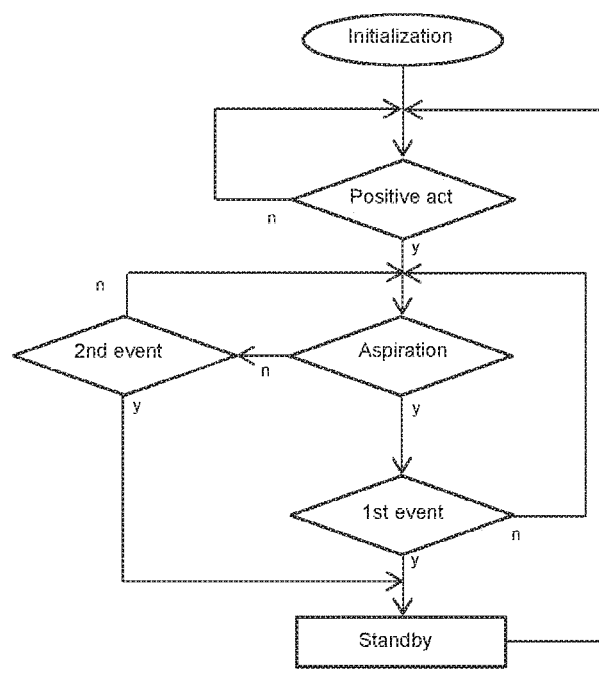
FIG. 3: improved basic flowchart.

A decision can also be made on a second event to be controlled, identical to or different from the first event, and as soon as this second event has occurred, the microprocessor causes the e-cigarette to go into standby. The control of this second event can take place during pauses between two successive aspirations (FIG. 3). In the flowchart of FIG. 3, the first control of the basic method (monitoring of a first event in step (c)) is completed by a second control during the pauses between each puff. For this purpose, in step (b), after each test that has concluded to the absence of aspiration, that is to say, during each pause between two successive puffs or between activation and the first puff, a second control event, identical to or different from the first control event, is monitored, and the method continues directly to step (d) if the second control event has occurred.

A first objective of the invention is that the e-cigarette goes into standby after the equivalent of the consummation of a traditional cigarette has been reached. It is thus provided to determine an event that reflects the total consumption of tobacco in a traditional cigarette. Here, the same event is controlled during the aspirations and during pauses.

Another objective of the invention is to provide a method of controlling an electronic inhaler serving to administer precise doses of medicaments. A decision is made on an event to be controlled (administration of the fixed dose) and as soon as this dose is reached, the microprocessor causes the inhalation device to go into standby (FIG. 2). Here, the control of the amount administered is performed only during aspirations. However, automatic placement on standby can be provided after a pause that is too long or a duration of administration that is too long (FIG. 3). In this case, the first controlled event (dose to be administered) is different from the second controlled event (duration of the pause is too long).

Depending on the intended applications, or on the desired complexity, various parameters can be taken into account by the method.

A first variant intended for inhalation devices serving as tobacco substitutes can provide that the step (c) comprises the following substeps:

(c1) determining the generated volume of aerosol (Vfum(i)) during the present step (c), (c2) calculating the cumulative volume of aerosol (Vcum(i)) by adding, to the cumulative volume (Vcum(i−1)) during the preceding step (c), the generated volume of aerosol (Vfum(i)) during the present step (c), wherein the cumulative volume (Vcum(0)) at the time of activation of the inhalation device has the value 0, and (c3) comparing the cumulative volume (Vcum(i)) to a predefined threshold volume (Vcig), the method then continuing at the beginning of step (b) if the cumulative volume (Vcum(i)) is less than the threshold volume (Vcig), or the method continuing at step (d) if the cumulative volume (Vcum(i)) is greater than or equal to the threshold volume (Vcig).

This simple method takes into consideration only the aerosol volume actually generated.

In a first, simple embodiment, the first event to be monitored in step (c) and the second event to be monitored in step (b) can be a predetermined duration of use. When the duration of use has been reached, the e-cigarette goes into standby. The duration of use can match the average time needed to smoke a traditional cigarette. Thus, a decision is made on a given number of units of time. When all these units of time have been used up, the e-cigarette goes into standby. In an alternative embodiment, it can be provided that an aspiration consumes more units of time than a pause.

Other examples of such methods are disclosed in the flowcharts of FIGS. 4 to 7. These more complex methods determine, not only the volume of aerosol generated during each aspiration, but also (i) the volume of aerosol fictitiously generated during each pause, (ii) the duration of the pause, and/or (iii) the time between two successive activations, or between the placement on standby and the next activation.

Between two aspirations, an e-cigarette does not use e-liquid and does not generate any aerosol, whereas a traditional cigarette burns slowly, which reduces the amount of tobacco available for smoking. Similarly, in a variant embodiment, fictitious volumes of aerosol can be calculated in addition to the volumes of aerosol actually generated during aspirations. Throughout the method, the volumes of aerosol generated and the fictitious volumes are added, and then this cumulative volume is compared to a threshold volume corresponding to the total volume of smoke that a traditional cigarette is likely to provide. As soon as the accumulated volume reaches or exceeds this threshold volume, the e-cigarette is placed on standby.

The method could calculate the generated volumes of aerosol and the fictitious volume at the end of each aspiration or of each pause, and then calculate the cumulative volume but compare it to the threshold value only at the end of each aspiration and of each pause. The drawback of this solution lies notably in the fact that, if the vaper forgot his e-cigarette, the e-cigarette is at the stage of a pause and will not go into standby, since it will not pass the test of the cumulative volume. So it is better to do the calculations and the tests continuously.

For this purpose, the microprocessor is clocked by the clock. The number of clock cycles depends on the frequency of the clock. For a frequency of 25 Hz, there are 25 clock cycles per second. In other words, the clock gives a pulse every ¹⁄₂₅th of a second. The microprocessor will use one or more clock cycles to perform a calculation, carry out a test, or measure a physical quantity. Therefore, each cell of a flowchart will require a given number of clock cycles. The microprocessor thus requires a certain time (time period) to pass from a particular point to another particular point of the flowchart, and to go through a series of instructions corresponding to a certain step of the method. The duration of these time periods depends on each step. The method will constantly go through the flowchart, even when it is on standby awaiting activation. Thus, at each aspiration, the method will go X times through the succession of steps (b) Aspiration=yes and (c) calculation of the aspirated volume+ calculation of the cumulative volume and return to the test to detect aspiration, then it will go X times through the test of step (b) Aspiration during a pause. For clarity reasons, the passage at each actual step is given the value (i) whether it is a step (a), (b) or (c), the preceding step (a), (b) or (c) being the step (i−1). A step (a) can follow a step (a) or a step (d), a step (b) can follow a step (a), a step (b) or a step (c), and a step (c) can follow a step (b) or a step (c) or even a step (a) when steps (a) and (b) are combined. Therefore the step (i−1) above or the step (i+1) following the current step (i) is not necessarily the same step. In the following, the general term "step passage . . . " will be used to discuss the passage in one of the steps.

After activation of the e-cigarette, the processor will test the presence of an aspiration until it detects one.

The fictitious volume (Vcn(i)) generated at each passage (i) in step (b) when the absence of an aspiration has been determined (thus, during a pause) is substantially constant. It is set at a reference value (Vcn). The volume of aerosol generated at each passage (i) in step (c) during an aspiration depends on the aspiration power (Pasp(i)) and on the temperature of the resistance (Tres(i)), both measured for this passage (i) of step (c). During pauses or in standby mode, the longer the pause lasts, the more the resistance cools down. Thus, at the beginning of aspiration, the resistance does not always have the same temperature, depending on whether it is a first aspiration (starting temperature=room temperature), an aspiration following a pause of average duration (low residual temperature), or an aspiration following the previous aspiration very closely (high residual temperature). Furthermore, the longer the duration of the aspiration, the more the resistance heats up. It is thus preferable to take into account the temperature of the resistance in the determination of the generated volume of aerosol. This temperature (Tres(i)) can be measured directly using a sensor or it can be estimated using other, more easily measurable parameters. For example, the temperature (Tres(i)) during aspiration can be estimated using the temperature estimated at the preceding step passage (i−1) (Tpreres=Tres(i−1)), to which is added a factor dependent on the aspiration power (Pasp(i)) and on the voltage at the terminals of the battery (Ubat(i)) during the present passage (i) of step (c). The temperature (Tres(i)) during a pause is estimated as a function of the temperature estimated at the preceding step passage (i−1) (Tpreres=Tres(i−1)) to which is subtracted a factor dependent on the temperature estimated at the preceding step passage (i−1) (Tpreres=Tres(i−1)). It is understood that the preceding step passage (i−1) can be a passage of step (a), a passage of step (b) or a passage of step (c).

For these calculations and estimations, tables or charts are prepared, which indicate, for each step passage (i), the estimated value as a function of the variable parameters selected. For example, for estimating the temperature of the resistance (Tres(i)) during aspiration, to the initial temperature (Tpreres=Tres(i−1)) estimated at the preceding step passage (i) is added a temperature delta read in the table as a function of the voltage at the terminals of the battery and of the aspiration power (Pasp(i)). A new estimated temperature (Tres(i)) for the present step passage (i) is obtained, which in turn serves as the estimated initial temperature (Tpreres(i+1)=Tres(i)) for the next step passage (i+1). During a pause, from the initial temperature (Tpreres=Tres(i−1)) estimated at the preceding step passage is subtracted a temperature delta read in a table as a function of the initial temperature (Tpreres=Tres(i−1)). Thus, a new estimated temperature (Tres(i)) for this step passage (i) is obtained, which in turn serves as the initial temperature (Tpreres(i+1)=Tres (i)) for the next step passage (i+1). The initial temperature at the activation of the e-cigarette is set to a predetermined value (Tini). Starting there, the temperature remains at this value until the first aspiration. It then increases at each of the passages of step (c) by a variable delta read in the table of aspirations, until the end of the aspiration. After the end of the aspiration, the temperature of the end of aspiration is decreased at each of the passages of step (b) without aspiration by a variable delta read in the table of pauses, until the beginning of the next aspiration. The same happens during the standby mode until a threshold value is reached, for example, the initial temperature (Tini). This control during the standby mode allows, if a vaper reactivates the e-cigarette very soon after it went into standby, to take into account the residual temperature of the resistance which has not had time to cool completely. The control resumes at the residual temperature and not to at the original temperature, so that overheating can be avoided.

The procedure to calculate the volumes of aerosol is similar. Upon activation of the e-cigarette, the generated volume of aerosol (Vfum(0)) and the cumulative volume (Vcum(0)) are set to zero. At each passage (i) of step (c) during the aspiration, the generated volume (Vfum(i)) is calculated on the basis of a value read in a table of generated volumes as a function of the aspiration power (Pasp(i)) and of the temperature of the resistance (Tres(i)). This generated volume (Vfum(i)) is added to the cumulative volume (Vcum (i−1)) calculated during the preceding passage (i−1) of step (b) or (c). For pauses, the fictitious volume (Vcn) is constant for each passage of step (b) that has determined the absence of an aspiration if the time periods required for the passage of these steps (b) have identical durations. The cumulated volume at the end of each passage of a step (b) without aspiration is thus increased by (Vcn).

The temperature of the resistance can also be used to limit heating of the atomizer in order to prevent overheating of the e-liquid, which could lead to the generation of harmful products. Thus, among the controls during the aspirations, it can be provided to compare the temperature of the resistance (Tres(i)) to a threshold value (Tmax). If the temperature (Tres(i)) is greater than the threshold value (Tmax), then heating of the atomizer is limited so that this threshold temperature (Tmax) is not exceeded.

In practice, heating of the resistance is performed by pulse width modulation (PWM) as a function of the aspiration power. The more powerful the aspiration, the larger the pulse width and the more the resistance will heat up. A frequency will be used that is much higher than for carrying out the method. For example, a frequency of 1,000 Hz can be chosen for the modulation.

If the vaping device is equipped with a light source such as a LED, the LED lights up during each aspiration. It can also be provided that the stronger the aspiration, the higher the light intensity of the LED. For this purpose, the power supply to the LED can be done, like to the resistance, by PWM as a function of the aspiration power. Here also, the more powerful the aspiration, the larger the pulse width and the more the LED will light up. This function simulates the embers of a cigarette which are more or less luminous depending on the aspiration power. By choosing a modulation frequency of 1,000 Hz, it is ensured that the eye does not perceive the very rapid succession of lit stages and off stages. It can also be provided that the LED is not switched off directly at the end of aspiration, but goes out progressively.

The vaping device can be activated in different ways. A switch can be provided. Also, it can be provided that the e-cigarette is activated only after it has been taken out of a casing designed for this purpose. This requires that the e-cigarette is stored again in its casing between two uses. For this purpose, it is expected that the e-cigarette communicates in "full-duplex" mode with the casing when it is inserted in it. The e-cigarette can, for example, receive data from the casing via the charging voltage, by amplitude modulation while the e-cigarette transmits its data to the casing, for example, by light pulses using the diode. In this case, the casing is provided with an optical sensor. It goes without saying that any other mode of communication may be considered, such as radio communication or communication by induction. When the e-cigarette is stored in the casing, it sends all its data to a memory located in the casing. A screen can be provided on the casing to show some data, such as the number of e-cigarettes vaped during the day, for example. Such a display can also be provided directly on the e-cigarette. The casing itself can communicate with a central unit, such as a smartphone or a computer, to allow further exploitation of the data. The screen makes it possible to display statistical data, such as, for example, the number of e-cigarettes smoked in the day, or the amount of medication or nicotine absorbed in the day. The unit of time can be the day, the week, the month, or any other unit significant for the vaper or the patient.

Another solution is to activate the e-cigarette at the first aspiration, or alternatively, when a heat source, for example the flame of a lighter, is approached to a heat detector located in the e-cigarette. This way, the gesture of "lighting" a cigarette is maintained. In all cases, a voluntary act of the vaper is required, which make him conscious that he is starting a new e-cigarette.

It is also possible to provide that the e-cigarette cannot be reactivated until a certain time has elapsed since the last standby or since the last activation. This prevents bypassing the objective of the method.

Thus, it is seen that the steps follow one another and are repeated several times.

Figure 4:
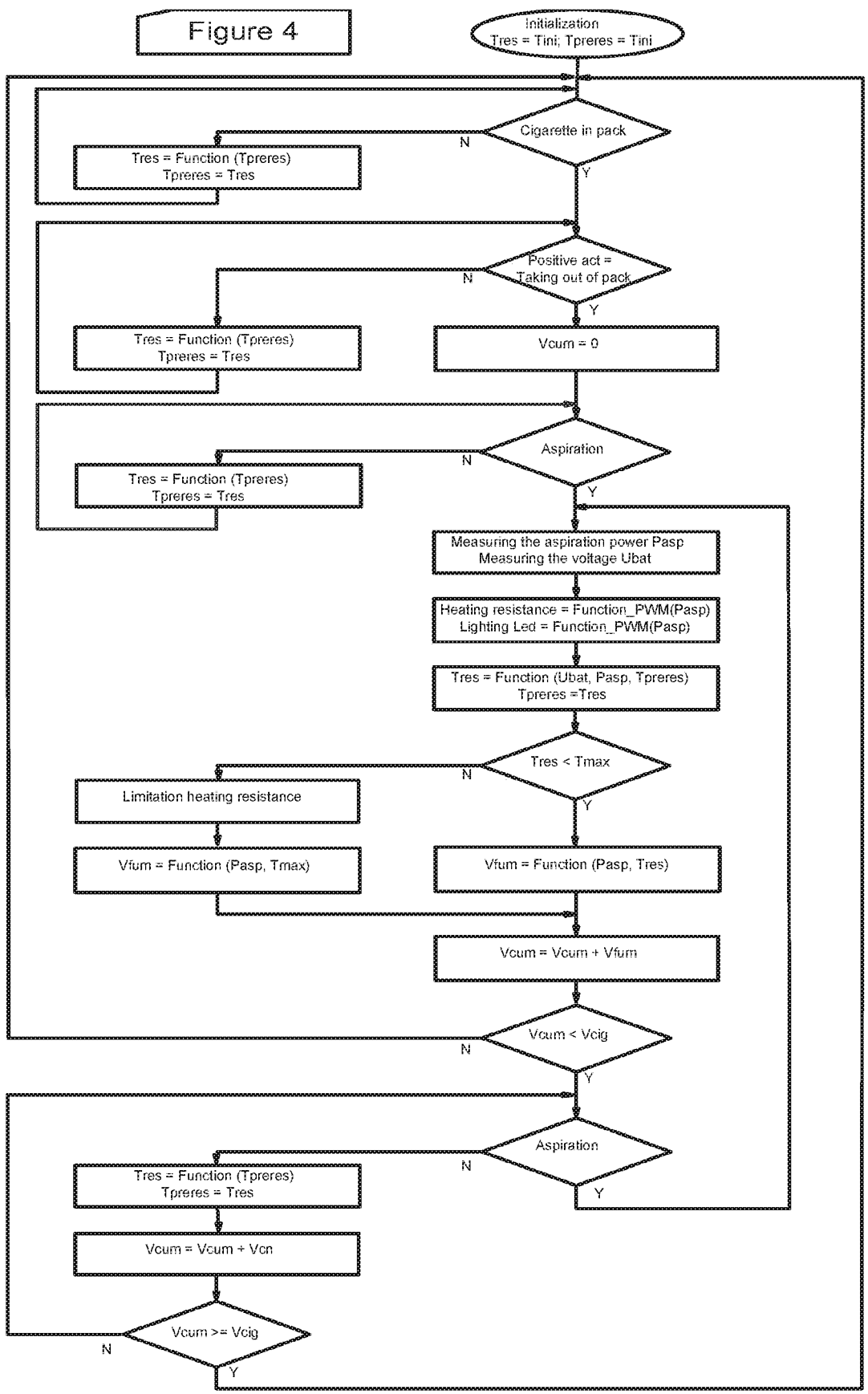
FIG. 4: detailed flowchart for an activation by removal from a casing.

The flowchart of FIG. 4 will now be explained in more detail. In this flowchart, it is provided as a positive act to take the cigarette out of its casing. This also means that it must be put back in its casing when it has gone into standby mode.

Preliminary Step

At first, either when purchasing it or following the end of a previous cycle, the e-cigarette is in standby mode. It is not possible to generate the aerosol, even by drawing a puff.

The positive act in this embodiment consists in taking the e-cigarette out of its casing. This means that it must have been placed in the casing in advance, either at the time of purchase or at the end of the previous cycle. Thus, there is a first loop consisting in testing the presence of the e-cigarette in its casing. As long as the micro-processor (control unit) determines that the e-cigarette is not in its casing, it continues to calculate the temperature of the resistance, which may be cooling down if its passage into standby mode is recent, or which may have reached the lower threshold value (Tini).

Step (a)

The first step consists in activating the e-cigarette, which for the moment is in standby mode, if a predetermined positive act has been detected. At regular intervals dependent on the frequency of the microprocessor, the performance of this positive act is tested until it has occurred. In the present example, the positive act consists in taking the e-cigarette out of its casing.

As long as the microprocessor determines that the e-cigarette is not out of its casing, it continues to calculate the temperature of the resistance.

When it determines that the e-cigarette has been taken out of the casing, the e-cigarette is activated and the cumulative volume (Vcum(0)) is reset to 0.

Step (a) of the method is completed.

1st Passage Through Step (b)

The method then monitors whether an aspiration is underway. This test is repeated until an aspiration is detected. As long as the microprocessor determines the absence of an aspiration, it continues to calculate the temperature of the resistance. As soon as an aspiration is detected, the first passage through step (b) of the method is completed and the first passage of step (c) begins. Thus, it usually takes several passages of step (b) without aspiration before passing through this step (b) and reaching step (c) for the first time.

1st Passage of Step (c)

To simplify the explanation of the flowchart, the setting is fixed at i=1 for the first passage of step (c) following the first aspiration, which ignores (for this explanation) all the passages of steps (a) and (b) before the first passage in step (c).

During the first passage of step (c) (i=1) of this first aspiration, the aspiration power (Pasp(1)) and the voltage at the terminals of the battery (Ubat(1)) are measured. Heating of the resistance of the atomizer is started and the LED is lit. For this purpose, these two components are supplied by a signal whose pulse width is modulated as a function of the aspiration power (PWM(Pasp)). The more powerful the aspiration, the larger the impulsion and the more the resistance will heat up and the LED will shine. By choosing a modulation frequency of 1,000 Hz, for example, the rapid succession (every 1/1,000 second) of switching the LED on and off will remain unnoticed to the human eye.

The temperature of the resistance is determined on the basis of the value of the temperature (Tpreres(1)=Tres(0)) at the preceding step passage (i=0), that is to say, the last temperature determined before detection of the aspiration, and on the basis of the voltage at the terminals of the battery (Ubat(1)) and of the aspiration power (Pasp(1)). This value Tres(1) is assigned to the value of the initial temperature (Tpreres(2)) for the next step passage (i=2).

To avoid overheating the atomizer, it is preferable to control its temperature and to limit its heating when this temperature exceeds a threshold value (Tmax). The method thus compares the temperature of the resistance (Tres(1)) to the threshold value (Tmax). If this value is exceeded, heating of the atomizer is limited.

The volume of aerosol generated during the first passage of this first aspiration (Vfum(1)) is determined in step (c1) as a function of the aspiration power (Pasp(1)) and of the estimated temperature (Tres(1)) or the threshold temperature (Tmax) if the temperature has exceeded this threshold.

In step (c2), the cumulative volume of aerosol (Vcum(1)) is calculated by adding, to the cumulative volume reset in step (a), and therefore equal to zero, the generated volume (Vfum(1)) calculated for this first passage of step (c) (i=1).

In step (c3), the cumulative volume (Vcum(1)) is compared to the threshold volume (Vcig) corresponding to the total volume of smoke likely to be provided by a corresponding traditional cigarette.

If the threshold volume (Vcig) is not reached (which should be the case here because it is the first passage of step (c) after the first aspiration after activation), the method returns to the beginning of step (b), namely, the test to determine whether there is still an aspiration.

If the cumulative volume (Vcum(1)) is greater than the threshold volume (Vcig), which in principle should not be the case at this stage of the vaping, the method proceeds to step (d).

The first passage of step (c) is completed this way.

Subsequent Passages of Step (b)

Due to the very short time period between two successive tests (time period imposed by the frequency of the clock and by the number of actions performed during each step (c)), the method should detect that an aspiration is still on-going, and return to a second passage of step (c). The method therefore proceeds to the step labeled "Subsequent passages of step (c)." This is also the case in the following passages of step (b) as long as an aspiration is detected during the test of step (b), or else in the subsequent steps (c) following a test that has determined that a new aspiration is taking place.

If the method detects, during a passage of step (b), that there is no longer an aspiration, for example, after X positive passages of the test, the vaper has now ceased to aspirate. In this case, the method provides the following steps for the present passage (i) of step (b):

determining the temperature of the resistance (Tres(i)) as a function of the initial temperature (Tpreres(i)=Tres (i−1)) determined during the preceding step passage (i−1) and assigning the current temperature (Tres(i)) to the initial value (Tpreres(i+1)) for the next step passage (i+1);

during a step (b1), determining a fictitious volume of aerosol (Vcn(i)). In practice, if the periods of time required to pass through step (b) have constant or substantially constant durations, this volume can also be considered constant (Vcn) for each passage of step (b);

during a step (b2), calculating the cumulative volume (Vcum(i)) of the generated volumes of aerosol (Vfum (i)) during the previous aspirations (calculated in the previous steps (c1)) and of the fictitious volumes (Vcn (i)) generated during pauses (calculated in the previous steps (b1)). Concretely, to the cumulative volume (Vcum(i−1)) of the preceding step passage is added the fictitious volume (Vcn(i)) determined in the present passage of step (b); then during a step (b3), comparing the cumulative volume (Vcum(i)) of the present passage of step (b) to the predetermined threshold volume (Vcig). If the cumulative volume reaches or exceeds the threshold volume (Vcig), the method continues to step (d), otherwise it returns to the beginning of step (b), namely, the test to determine the presence of an aspiration.

The subsequent step b is completed

Subsequent Passages of Step (c)

The method has detected during one of the passages of step (b) that the aspiration was continuing, or that a new aspiration was beginning.

The aspiration power (Pasp(i)) and the voltage at the terminals of the battery (Ubat(i)) are measured. Heating of the resistance of the atomizer is started and the LED is lit, both still being fed by a signal whose pulse width is modulated as a function of the aspiration power (PWM(Pasp (i)).

The temperature of the resistance is determined by adding, to the preceding temperature (Tpreres (i)=Tres(i−1)), a delta calculated as a function of the voltage at the terminals of the battery and of the power of the aspiration (Pasp(i)). The value of the current temperature (Tres(i)) is assigned to the initial temperature (Tpreres(i+1)) for the next step passage.

In order to avoid overheating of the atomizer, its temperature can be controlled and its heating limited when the temperature exceeds a threshold value. Thus, the method compares the temperature of the resistance (Tres(i)) to a threshold value (Tmax). If this value is exceeded, heating of the atomizer is limited.

During another passage of step (c1), the generated volume of aerosol (Vfum(i)) is determined as a function of the aspiration power (Pasp(i)) and of the temperature of the resistance (Tres(i)) or the threshold temperature (Tmax) if the temperature has exceeded this threshold.

During a new passage of step (c2), the cumulative volume (Vcum(i)) is calculated by adding, to the preceding cumulative volume (Vcum(i−1)), the generated volume of aerosol (Vfum(i)) during the present passage of step (c). During a new passage of step (c3), the cumulative volume (Vcum(i)) is compared to the threshold value (Vcig). If the threshold value is not reached, the method returns to the beginning of step (b), namely, the test to determine the presence of an aspiration, otherwise it proceeds to step (d).

Step (d)

Step (d) is reached as soon as the cumulative volume (Vcum(i)) reaches or exceeds the threshold volume (Vcig) for this type of cigarette. The method is completed and the e-cigarette goes into standby mode. It will not work again until after it will have been stored in its casing and then taken out (see preliminary step). This gesture of taking out the e-cigarette from its casing is designed to make the vaper conscious of the number of "cigarettes" that he smokes.

It is also possible to put the e-cigarette back in the casing before it has gone into standby mode. This is not dangerous, because the resistance heats up only when the method detects an aspiration. Because of the calculation of the fictitious volume, it will automatically go into standby mode after a certain time.

The method described in this flowchart provides various possible options. However, it would be possible to calculate the generated volume of aerosol (Vfum(i)) without taking into account the aspiration power (Pasp(i)) and/or the temperature of the resistance (Tres(i)). In a very simple variant, it could be considered that the e-cigarette generates, for each passage of step (c), a volume of aerosol (Vfum) that is constant when there is aspiration, and, for each passage of step (b), a fictitious volume (Vcn) that is constant and less than (Vfum). It would even be possible to renounce determining a fictitious volume during pauses. Instead of the test of the cumulative volume during pauses, a test of the duration of aspiration or duration of the pause, at the end of which the e-cigarette is placed on standby, could be introduced. If the vaping device is equipped with a temperature detector, it is no longer necessary to evaluate the temperature.

Figure 5:
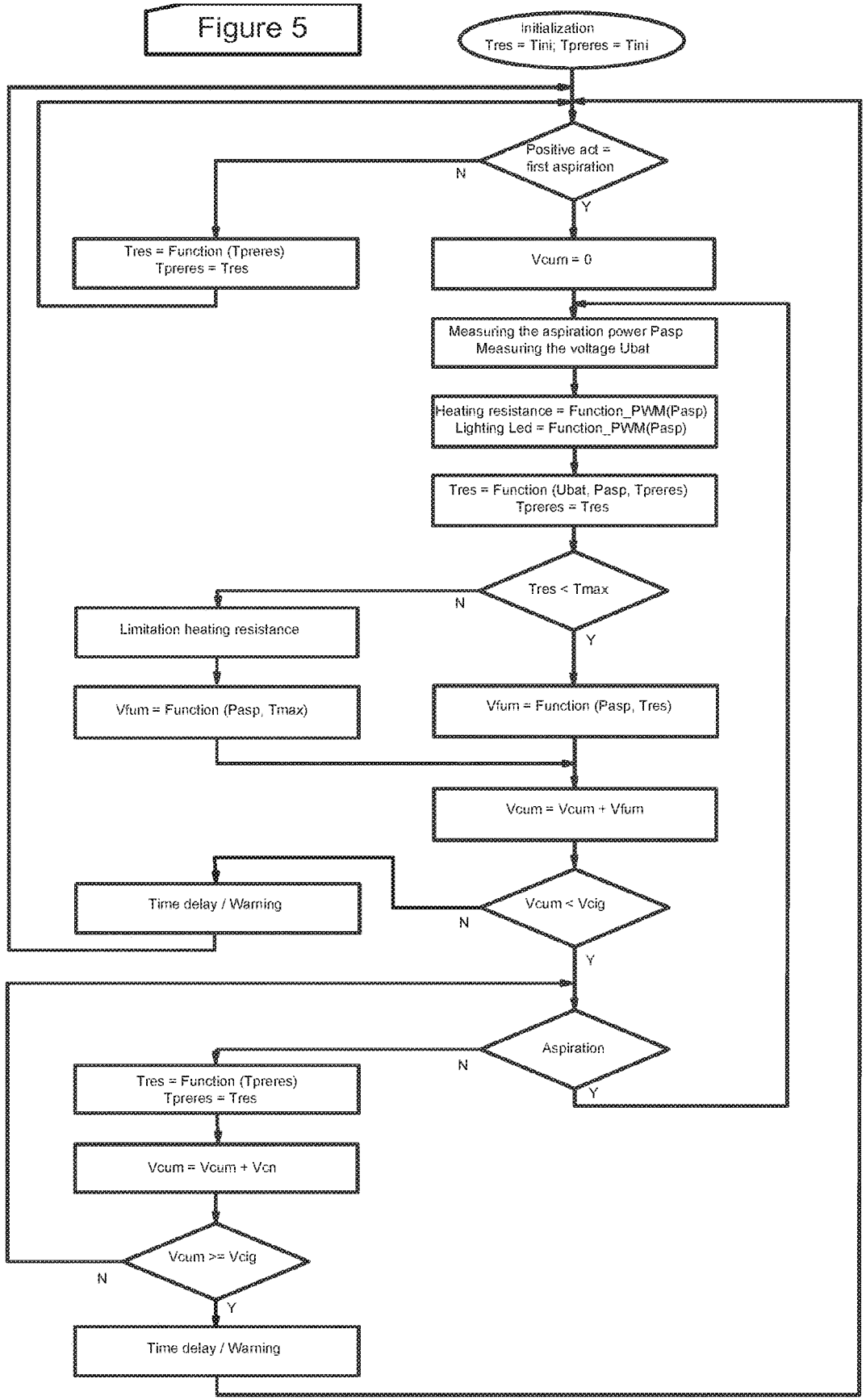
FIG. 5: detailed flowchart for activation by a first aspiration.
Figure 6:
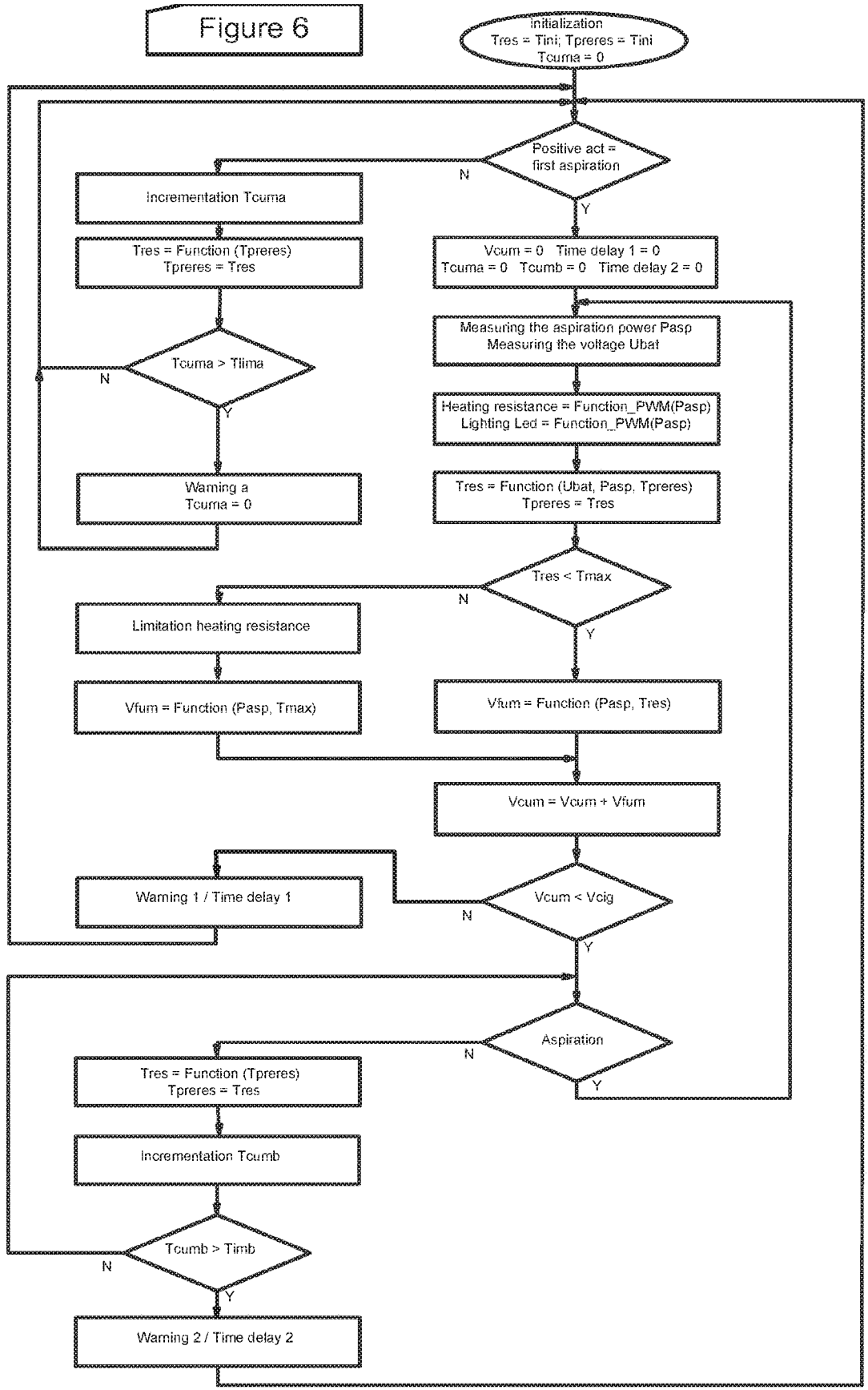
FIG. 6: detailed flowchart for administering a medicament with activation by a first aspiration.

The methods of FIGS. 5-7 operate in substantially the same manner. They are distinguished from the first example in particular by the positive act and by the introduction of one or more time delays.

The method of FIGS. 5 and 6 is triggered when the microprocessor detects a first aspiration after entry into the standby mode. The steps are essentially identical to those of the method of FIG. 4. Thus, they are only mentioned, without going into details.

Step (a)/First Passage of Step (b)

Here, the positive act is constituted by the first aspiration after entry into the standby mode. As long as no aspiration is detected, the microprocessor continues to calculate the temperature of the resistance.

As soon as the first aspiration is detected, the e-cigarette goes into the activated mode and the cumulative volume (Vcum(0)) is reset to 0. Step (a) and the first passage of step (b) are completed, and the method passes directly to step (c) since an aspiration has been detected.

Subsequent Passages of Step (b)

In the rest of the method, as long as no aspiration is detected, the microprocessor continues to calculate, for each passage (i) of step (b), the temperature of the resistance (Tres(i)). It also calculates the fictitious volume (Vcn(i)) that it adds to the preceding total, and it compares the current total to the threshold value (Vcig). If this threshold value is reached, the method proceeds to step (d), otherwise it returns to the beginning of step (b) and tests for the presence of an aspiration.

When an aspiration is detected, the method proceeds to step (c).

Step (c)

The aspiration power (Pasp(i)) and the voltage at the terminals of the battery (Ubat(i)) are measured. The resistance and the LED are switched on using a signal whose pulse width is modulated as a function of the aspiration power (Pasp(i)). The temperature of the resistance (Tres(i)) is calculated as a function of the preceding temperature (Tprésres(i)=Tres(i−1)), of the voltage at the terminals of the battery (Ubat(i)), and of the aspiration power (Pasp(i)). This value (Tres(i)) is assigned to the initial temperature (Tpreres(i+1)) for the next step passage. The temperature is compared to the threshold value (Tmax) and heating of the resistance is limited if this temperature is reached or exceeded. The generated volume of smoke (Vfum(i)) is calculated as a function of the aspirated power (Pasp(i)) and of the temperature of the resistance (Tres(i)) or the threshold temperature (Tmax) if this threshold is reached or exceeded. The cumulative volume (Vcum(i)) is calculated by adding, to the preceding cumulative volume (Vcum(i−1)), the generated volume of smoke (Vfum(i)) calculated for the present passage of step (c). This cumulative volume (Vcum(i)) is compared to the threshold value (Vcig). If this value is reached or exceeded, the method continues to step (d), otherwise it returns to step (b) consisting in detecting the presence of an aspiration.

Step (d)

In order to prevent a vaper from bypassing the objective of the method which is to make him conscious that he is lighting a new cigarette, it can be provided that the first aspiration that makes the e-cigarette go from the standby state to the activated state cannot take place until a certain time has elapsed. It has therefore been provided, in step (d), to trigger a time delay before switching to the standby mode. As long as the cumulative time between the passage in standby mode has not reached a threshold value (Delay1), it is not possible to pass the test of step (a), i.e., to detect the positive act, here, the first aspiration. It is also provided to emit a signal at the beginning of the time delay to inform the user or a third party, or even a process for managing this time delay. The decrease in temperature of the resistance continues to be calculated during the entire time delay (Delay1).

The method of FIG. 6 is a variant of that of FIG. 5. This method is applied to an inhalation device for administration of a medicament. The method does not calculate a fictitious volume (Vcn) any more. In contrast, two time delays (Delay1, Delay2) for preventing the reactivation of the inhalation device before the scheduled time, a regular reminder (tcum$_a$) to the patient after completion of the time delays (Delay1, Delay2) so that he takes his medicament, and a control of the cumulative duration of the pauses between two aspirations (tcum$_b$) are provided. The control of the cumulative duration of the pauses (tcum$_b$) is used to limit the time available to administer the drug. Past the authorized time (tlim$_b$), the inhalation device goes into standby mode automatically, even though the full dose has not been administered. The time delays (Delay1, Delay2) serve to prevent the reactivation of the device as long as a minimum time interval has not elapsed since the last activation or the last standby. This allows controlling the time interval between two intakes. These time delays can be triggered at the end of the preceding cycle as in the method of FIG. 5, or at the beginning of the preceding cycle. A first time delay (Delay1) is triggered when the drug intake is completed (Vcum(i)≥Vcig), while a second time delay (Delay2) is triggered when the cumulative duration of pauses has exceeded the threshold time (tcum$_b$≥tlim$_b$). It can be provided that a signal is emitted, not only when the device goes into standby mode, but also when the interval between two intakes is completed. The signal (Warning1) emitted at the passage into standby mode following the complete intake of the drug (Vcum(i)≥Vcig) can be different from the signal (Warning2) emitted when the time allowed for taking the medication is completed without the totality of the dose having been taken (tcum$_b$≥tlim$_b$). When both time delays (Delay1, Delay2) are used, the method provides that during the placement on standby of the inhalation device following the expiration of the authorized time for taking a dose, the second time delay (Delay2) then takes into account the times of pauses (tcum$_b$(i)), and notably that the duration of the second time delay (Delay2) is equal to the duration of the first time delay (Delay1) minus the cumulative duration of the pauses (tcum$_b$(i)).

In step (a) and in the first step (b), the method controls whether a first aspiration is detected. As long as no aspiration is detected, the microprocessor continues to calculate the temperature of the resistance and it monitors the time spent in this loop. As long as a first aspiration is not detected, the duration (t(i)) of each passage (i) is determined and the cumulated total (tcum$_a$(i)) is calculated. Each time this total reaches or exceeds a threshold duration (tlim$_a$), a signal is emitted (Warning a) and the total is reset to 0 (tcum$_a$(i)=0). In practice, all the passages of this step have the same duration. Thus, the patient is regularly reminded that he must take his medication dose if he has not already done so.

As soon as the first aspiration is detected, the e-cigarette goes into activated mode and the cumulative volume (Vcum(0)), the total of the waiting time (tcum$_a$(i)) and of the intake duration control (tcum$_b$(i)) are reset to 0, as well as the blocking time delays (Delay1, Delay2). Step (a) and the first passage of step (b) are completed.

At each passage of step (b), that is to say, each time the method determines that there is no aspiration, the temperature of the resistance (Tres(i)) is calculated as a function of the preceding temperature (Tpreres(i)=Tres(i−1)). Similarly, during a step (b1'), the duration (t(i)) of the present passage of step (b) is determined. In practice, all the passages in step (b) have the same duration. Then, in a step (b2'), the cumulative duration of the pauses (tcum$_b$(i)) in the present passage (i) of step (b) is calculated by adding, to the previous total ($tcum_b(i-1)$), the duration of the present step passage ($t(i)$). In a step (b3'), the cumulative duration of the pauses ($tcum(i)$) is compared to a threshold duration ($tlim_b$). If the time authorized to take the medication has not expired, the method returns to the beginning of step (b), that is to say, to the test to detect the aspiration, otherwise it continues to step (d).

At each passage of step (c), the total of the durations of the pauses ($tcum_b(i)$), which controls the time authorized to take a dose, is kept and remains unchanged.

It can be provided that a signal is emitted when the device goes into standby mode after intake of the totality of the dose ($Vcum(i) \geq Vcig$) and/or when the device goes into standby mode at the end of the time authorized to take the dose without the dose having been taken in its totality ($tcum_b(i) \geq tlim_b$) and/or at the end of the interval between two intakes (Delay1, Delay2). These signals can be identical or different.

The method of FIG. 7 is triggered when the vaper presses a button or "lights up" his e-cigarette with the flame of a lighter. The method is almost the same as in the case where the e-cigarette must be stored in its casing before it is possible to reactivate the e-cigarette. The difference lies mainly in the absence of a control of the presence of the e-cigarette in the casing. When the e-cigarette must be lighted with a flame, it is preferable to equip the electronic cigarette with a heat detector, in particular an infrared sensor.

Other variants of the method are possible by combining differently some of the various following options:
- time delay between two reactivations;
- time delay between the placement on standby and the next reactivation;
- emission of a signal each time an event has occurred;
- calculation of the fictitious volumes;
- calculation of the temperature of the resistance; etc.

The signals emitted during the method can be sensory signals, such as light or acoustic signals, or they can be messages of the text or email type sent to the user or to a third party, or signals intended for a management or control process.

INDUSTRIAL APPLICABILITY POSSIBILITIES

The method of the invention, applied to a substitute for a tobacco product, such as an electronic cigarette, allows the vaper to encounter signs similar to those he was familiar with during the consumption of traditional tobacco products. Because of the extinction of the vaping device when it goes into standby mode, he becomes aware of having finished a "cigarette". He does not risk to overdose unconsciously on nicotine, for instance.

Applied to the administration of a medicament, the device can control the interval between two intakes, as well as limit the time authorized to take the drug. It facilitates the management of the drug's administration.

LIST OF REFERENCES

1 Vaping device (e-cigarette)
2 Electrical power source (battery)
3 Aspiration power sensor
4 Control unit (microprocessor)
5 Cartomizer (combination of an atomizer and a reservoir)
51 Heating resistance of the atomizer or cartomizer
6 LED $Pasp(i)$ Power of the aspiration during the present passage (i) of step (c)
$Tres(i)$ Temperature of the resistance during the present step passage (i)
$Tpreres(i)$ Temperature of the resistance during the preceding step passage (i−1)
$Tini$ Initial temperature
$Tmax$ Limit temperature
$t(i)$ Duration of the present passage (i) of step (b)
$tcum_a(i)$ Total of the durations of the passages of step (a) elapsed while waiting for a positive act
$tlim_a$ Duration of the interval between two reminders in the event of non-activation
$tcum_b(i)$ Total of the durations of the passages of step (b) during the pauses
$tlim_b$ Time authorized to take a dose
Delay1 Time interval between two successive activations, or between a placement on standby and the next activation in the case of having reached the threshold volume
Delay2 Time interval between two successive activations, or between a placement on standby and the next activation in case of a pause being too long
$Ubat(i)$ Voltage at the terminals of the power source during the present passage (i) of step (c)
$Vfum(i)$ Volume of aerosol generated during the present passage (i) of step (c), i.e., in the case of an aspiration
$Vcn(i)$ Fictitious volume generated during the present passage (i) of step (b), i.e., in the case of a pause
$Vcum(i)$ Cumulative volume of the volumes of aerosol actually generated and fictitiously generated
$Vcig$ Threshold volume

The invention claimed is:

1. Method of controlling an inhalation device of a vaping type adapted to generate an aerosol by vaporization of a liquid by an atomizer, wherein the method comprises:
   (a) testing to detect activation of the inhalation device, and proceeding to step (b) as soon as the activation of the inhalation device is detected,
   (b) testing to detect a presence of an aspiration of a puff, and proceeding to step (c) as soon as the aspiration of the puff is detected,
   (c) monitoring a first control event during each puff, and returning to step (b) if the first control event has not occurred, or continuing to step (d) if the first control event has occurred,
   (d) placing the inhalation device on standby,
   wherein an aerosol can be generated in an event of an aspiration when the device is activated, but not when the device is on standby,
   wherein step (c) comprises the following sub-steps performed at each passage of step (c);
   (c1) determining a generated volume of aerosol ($Vfum(i)$) during the present passage (i) of step (c),
   (c2) calculating a cumulative volume of aerosol ($Vcum(i)$) by adding, to the cumulative volume ($Vcum(i-1)$) of the preceding passage of step (i−1), the generated volume of aerosol ($Vfum(i)$) during the present passage of step (c), wherein the cumulative volume ($Vcum(0)$) at the time of activation of the inhalation device has the value 0, and
   (c3) comparing the cumulative volume ($Vcum(i)$) to a predefined threshold volume ($Vcig$), the method then continuing at the beginning of step (b) if the cumulative volume ($Vcum(i)$) is less than the threshold volume ($Vcig$), the method continuing at step (d) if the cumulative volume ($Vcum(i)$) is greater than or equal to the threshold volume ($Vcig$).

2. Control method according to claim 1, wherein, in step (d), a signal is emitted when the inhalation device is placed on standby.

3. Control method according to claim 1, wherein, in step (b), after each test that has concluded to an absence of aspiration, a second control event, identical to or different from the first control event, is monitored, and the method continues directly at step (d) if the second control event has occurred.

4. Control method according to claim 1, wherein the inhalation device can be activated in step (a) only after a time interval, called blocking interval, has elapsed since the preceding placement on standby in step (d) or since the preceding activation in step (a), or since a predefined action was performed.

5. Control method according to claim 4, wherein, after expiry of the blocking interval, a signal is emitted at regular intervals, called reminder intervals, as long as the inhalation device has not been activated in step (a).

6. Control method according to claim 1, wherein step (b) comprises the following sub-steps performed at each passage of step (b) after each test of step (b) that has determined the absence of an aspiration:
(b1) determining a fictitious volume of aerosol ($Vcn(i)$) corresponding to the present passage (i) of step (b),
(b2) calculating the cumulative volume ($Vcum(i)$) of the volumes of aerosol generated previously during aspirations and of the fictitious volumes previously generated between two successive aspirations by adding, to the cumulative volume ($Vcum(i-1)$) of the preceding step passage (i−1), the fictitious volume of aerosol ($Vcn(i)$) of the present passage (i) of step (b), wherein the cumulative volume ($Vcum(0)$) at the time of activation of the inhalation device has the value 0,
(b3) comparing the cumulative volume ($Vcum(i)$) to the predefined threshold volume ($Vcig$), the method continuing at the beginning of step (b) if the cumulative volume ($Vcum(i)$) is less than the threshold volume, or the method continuing at step (d) if the cumulative volume ($Vcum(i)$) is greater than or equal to the threshold volume ($Vcig$).

7. Control method according to claim 6, wherein the fictitious volume of aerosol ($Vcn(i)$) by the passage of step (b) during the pauses is constant ($Vcn$) and/or wherein the cumulative volume ($Vcum(i)$) is calculated and compared to the threshold volume ($Vcig$) a plurality of times per aspiration and/or per pause between two successive aspirations.

8. Control method according to claim 1, wherein step (b) comprises the following sub-steps performed at each passage of step (b) after each test of step (b) that has determined an absence of an aspiration:
(b1') determining a duration ($t(i)$) of the present passage (i) of step (b),
(b2') calculating a cumulative duration ($tcum_b(i)$) of all the passages of step (b) during which the method determines the absence of an aspiration by adding, to the cumulative duration ($tcum_b(i-1)$) of the preceding passage (i−1) of step (b), the duration ($t(i)$) of the present passage of step (b), wherein the cumulative duration ($tcum_b(0)$) at the time of activation of the inhalation device has the value 0,
(b3') comparing the cumulative duration ($tcum_b(i)$) to a predefined threshold control duration ($tlim_b$), the method continuing at the beginning of step (b) if the cumulative duration ($tcum_b(i)$) is less than the threshold duration ($tlim_b$), or the method continuing at step (d) if the cumulative duration ($tcum_b(i)$) is greater than or equal to the threshold duration ($tlim_b$).

9. Control method according to claim 8, wherein the cumulative duration ($tcum_b(i)$) is calculated and compared to the threshold duration ($tlim_b$) a plurality of times per pause, and/or wherein, in step (b3'), when the method proceeds to step (d), a signal is emitted.

10. Method according to claim 1, wherein step (b) comprises the following sub-steps performed at each passage of step (b) after each test of step (b) that has determined an absence of an aspiration:
(b1') determining a duration ($t(i)$) of the present passage (i) of step (b),
(b2') calculating a cumulative duration ($tcum_b(i)$) of all the passages of step (b) during which the method determines the absence of an aspiration by adding, to the cumulative duration ($tcum_b(i-1)$) of the preceding passage (i−1) of step (b), the duration ($t(i)$) of the present passage of step (b), wherein the cumulative duration ($tcum_b(0)$) at the time of activation of the inhalation device has the value 0,
(b3') comparing the cumulative duration ($tcum_b(i)$) to a predefined threshold control duration ($tlim_b$), the method continuing at the beginning of step (b) if the cumulative duration ($tcum_b(i)$) is less than the threshold duration ($tlim_b$), or the method continuing at step (d) if the cumulative duration ($tcum_b(i)$) is greater than or equal to the threshold duration ($tlim_b$),
and wherein a first blocking time delay (Delay1) is provided after the placement on standby in step (d) when the cumulative volume ($Vcum(i)$) is greater than or equal to the threshold volume ($Vcig$), and a second blocking time delay (Delay2) is provided after the placement on standby in step (d) after expiry of the threshold control duration ($tlim_b$).

11. Control method according to claim 1, wherein in step (c1), an aspiration power ($Pasp(i)$) of the present passage (i) of step (c) is determined, and/or a temperature of the atomizer ($Tres(i)$) of the present passage (i) of step (c) is determined, the generated volume of aerosol ($Vfum(i)$) during the present passage (i) of step (c) is calculated based on the power of the aspiration ($Pasp(i)$) and/or of the temperature of the atomizer ($Tres(i)$).

12. Control method according to claim 1, wherein, at each passage (i) of step (c), a temperature of the atomizer ($Tres(i)$) is determined and compared to a threshold value ($Tmax$), wherein heating of the atomizer is limited if the temperature of the atomizer ($Tres(i)$) is greater than the threshold value ($Tmax$) and a volume of generated aerosol ($Vfum(i)$) during the present passage (i) of step (c) is calculated based on an aspiration power ($Pasp(i)$) and/or of the threshold temperature ($Tmax$).

13. Control method according to claim 1, wherein
before a first activation of the inhalation device,
a temperature of the atomizer ($Tres$) is set to an initial value ($Tini$);
during each aspiration, at each passage (i) of step (c),
an aspiration power ($Pasp(i)$) is determined,
a voltage ($Ubat(i)$) at terminals of an electric power source is measured,
the temperature of the atomizer ($Tres(i)$) is determined (i) as a function of the temperature of the atomizer ($Tres(i-1)$) at a preceding step passage (i−1) and (ii) as a function of the aspiration power ($Pasp(i)$) and of the voltage at the terminals of the power source ($Ubat(i)$);

during each pause between two aspirations and during the standby period, at each passage (i) of step (a) or (b), the temperature of the atomizer (Tres(i)) is determined as a function of the temperature of the atomizer (Tres(i−1)) at the preceding step passage (i−1).

14. Control method according to claim 1, wherein the inhalation device is equipped with a light source, the method comprising lighting up the light source during each aspiration.

15. Method according to claim 14, wherein a light intensity of the light source at each passage (i) of step (c) depends on an aspiration power (Pasp(i)) and/or the light source goes out gradually at an end of each aspiration and/or the light source is supplied with a signal whose pulse width is modulated (PWM).

16. Control method according to claim 1, wherein the activation of the inhalation device in step (a) is triggered by pressing a switch and/or automatically by taking the inhalation device out of a casing and/or at the first aspiration and/or after a heat source, has been approached to a detector present in the inhalation device.

17. Control method according to claim 1, wherein heating of the aerosol is controlled by a signal whose pulse width is modulated (PWM).

18. Control method according to claim 1, wherein the activation of the inhalation device in step (a) is triggered by taking the inhalation device out of a casing and a counter is provided which is incremented each time the inhalation device is put back into the casing after at least one aspiration has been detected.

19. Control method according to claim 1, wherein a counter is provided which is incremented each time the method passes in step (d).

20. Inhalation device comprising a source of electrical power, a reservoir for a liquid to be vaporized, an atomizer for vaporizing the liquid in order to generate an aerosol, an aspiration sensor and a control unit, wherein the reservoir and the atomizer can be combined into a single component, wherein the control unit is provided with means for implementing a method comprising:
    (a) testing to detect the activation of the inhalation device, and proceeding to step (b) as soon as the activation of the inhalation device is detected,
    (b) testing to detect a presence of an aspiration of a puff, and proceeding to step (c) as soon as the aspiration of the puff is detected,
    (c) monitoring a first control event during each puff, and returning to step (b) if the first control event has not occurred, or continuing to step (d) if the first control event has occurred,
    (d) placing the inhalation device on standby,
    wherein an aerosol can be generated in an event of an aspiration when the device is activated, but not when the device is on standby,
    wherein step (c) comprises the following sub-steps performed at each passage of step (c);
    (c1) determining a generated volume of aerosol (Vfum(i)) during the present passage (i) of step (c),
    (c2) calculating a cumulative volume of aerosol (Vcum(i)) by adding, to the cumulative volume (Vcum(i−1)) of the preceding passage of step (i−1), the generated volume of aerosol (Vfum(i)) during the present passage of step (c), wherein the cumulative volume (Vcum(0)) at the time of activation of the inhalation device has the value 0, and
    (c3) comparing the cumulative volume (Vcum(i)) to a predefined threshold volume (Vcig), the method then continuing at the beginning of step (b) if the cumulative volume (Vcum(i)) is less than the threshold volume (Vcig), or the method continuing at step (d) if the cumulative volume (Vcum(i)) is greater than or equal to the threshold volume (Vcig).

21. Inhalation device according to claim 20, wherein the device is provided with a screen adapted to display statistical information about an amount of generated volumes of aerosol (Vfum) during a predefined unit of time or a number of times the method has passed in step (d) per a unit of time.

22. Inhalation device according to claim 20, wherein the device is provided with a casing in which it can be stored, a screen being provided on the inhalation device and/or on the casing.

23. Device according to claim 22, wherein the screen is adapted to display statistical information about an amount of generated volumes of aerosol (Vfum) during a predefined unit of time or a number of times the method has passed in step (d) per a unit of time.

24. Device according to claim 23, wherein is equipped with a counter which is incremented each time the method passes in step (d).

25. Method according to claim 10, wherein the duration of the second time delay (Delay2) is equal to a duration of the first time delay (Delay1) minus the threshold control duration (tlim$_b$).

26. Method of controlling an inhalation device of the vaping type adapted to generate an aerosol by vaporization of a liquid by an atomizer, wherein the method comprises:
    (a) testing to detect activation of the inhalation device, and proceeding to step (b) as soon as the activation of the inhalation device is detected,
    (b) testing to detect a presence of an aspiration of a puff, and proceeding to step (c) as soon as the aspiration of the puff is detected,
    (c) monitoring a first control event during each puff, and returning to step (b) if the first control event has not occurred, or continuing to step (d) if the first control event has occurred,
    (d) placing the inhalation device on standby,
    wherein an aerosol can be generated in an event of an aspiration when the device is activated, but not when the device is on standby, wherein
    before a first activation of the inhalation device,
        a temperature of the atomizer (Tres) is set to an initial value (Tini);
    during each aspiration, at each passage (i) of step (c),
        an aspiration power (Pasp(i)) is determined,
        a voltage (Ubat(i)) at terminals of an electric power source is measured,
        the temperature of the atomizer (Tres(i)) is determined (i) as a function of the temperature of the atomizer (Tres(i−1)) at a preceding step passage (i−1) and (ii) as a function of the aspiration power (Pasp(i)) and of the voltage at the terminals of the power source (Ubat(i));
    during each pause between two aspirations and during the standby period, at each passage (i) of step (a) or (b),
        the temperature of the atomizer (Tres(i)) is determined as a function of the temperature of the atomizer (Tres(i−1)) at the preceding step passage (i−1).

27. Inhalation device comprising a source of electrical power, a reservoir for a liquid to be vaporized, an atomizer for vaporizing the liquid in order to generate an aerosol, an aspiration sensor and a control unit, wherein the reservoir and the atomizer can be combined into a single component, wherein the control unit is provided with means for implementing a method comprising:

(a) testing to detect activation of the inhalation device, and proceeding to step (b) as soon as the activation of the inhalation device is detected, (b) testing to detect a presence of an aspiration of a puff, and proceeding to step (c) as soon as the aspiration of the puff is detected, (c) monitoring a first control event during each puff, and returning to step (b) if the first control event has not occurred, or continuing to step (d) if the first control event has occurred, (d) placing the inhalation device on standby, wherein an aerosol can be generated in an event of an aspiration when the device is activated, but not when the device is on standby, wherein an aerosol can be generated in the event of an aspiration when the device is activated, but not when it is on standby, wherein before a first activation of the inhalation device, a temperature of the atomizer (Tres) is set to an initial value (Tini);

during each aspiration, at each passage (i) of step (c), an aspiration power (Pasp(i)) is determined, a voltage (Ubat(i)) at terminals of an electric power source is measured, the temperature of the atomizer (Tres(i)) is determined (i) as a function of the temperature of the atomizer (Tres(i−1)) at a preceding step passage (i−1) and (ii) as a function of the aspiration power (Pasp(i)) and of the voltage at the terminals of the power source (Ubat(i));

during each pause between two aspirations and during the standby period, at each passage (i) of step (a) or (b), the temperature of the atomizer (Tres(i)) is determined as a function of the temperature of the atomizer (Tres(i−1)) at the preceding step passage (i−1).

* * * * *